(12) United States Patent
Morad et al.

(10) Patent No.: US 10,192,386 B2
(45) Date of Patent: Jan. 29, 2019

(54) MECHANICAL TIME DELAY PRODUCT DISPENSER

(71) Applicant: The Tranzonic Companies, Cleveland, OH (US)

(72) Inventors: Fred I. Morad, Toluca, CA (US); Robert A. Acosta, Jr., Norwalk, CA (US)

(73) Assignee: The Tranzonic Companies, Cleveland, OH (US)

( * ) Notice: Subject to any disclaimer, the term of this patent is extended or adjusted under 35 U.S.C. 154(b) by 0 days.

(21) Appl. No.: 15/333,007

(22) Filed: Oct. 24, 2016

(65) Prior Publication Data
US 2018/0114396 A1    Apr. 26, 2018

(51) Int. Cl.
| | |
|---|---|
| *G07F 11/20* | (2006.01) |
| *A61F 15/00* | (2006.01) |
| *G07F 11/04* | (2006.01) |
| *G07F 11/10* | (2006.01) |
| *G07F 11/22* | (2006.01) |

(52) U.S. Cl.
CPC ............ *G07F 11/20* (2013.01); *A61F 15/001* (2013.01); *G07F 11/04* (2013.01); *G07F 11/10* (2013.01); *G07F 11/22* (2013.01)

(58) Field of Classification Search
CPC .... G07F 11/005; G07F 11/20; B65D 83/0033
See application file for complete search history.

(56) References Cited

U.S. PATENT DOCUMENTS

| | | | | |
|---|---|---|---|---|
| 2,078,984 | A * | 5/1937 | Williamson | ............ G07F 13/10 193/32 |
| 2,337,065 | A * | 12/1943 | Price | ...................... A47K 10/44 221/15 |
| 2,359,398 | A | 10/1944 | Thompson | |
| 2,369,851 | A * | 2/1945 | Price | ...................... A47K 10/38 226/121 |
| 2,816,760 | A * | 12/1957 | Seragnoli | .................. B65C 9/14 156/DIG. 31 |
| 2,940,720 | A * | 6/1960 | Birr | ........................ A47K 10/28 24/572.1 |

(Continued)

FOREIGN PATENT DOCUMENTS

| | | |
|---|---|---|
| CA | 2445203 A1 | 4/2005 |
| CA | 2463394 A1 | 4/2005 |

OTHER PUBLICATIONS

European Search Report, dated Dec. 21, 2017; 10 pages.
European Search Report; dated Dec. 8, 2017; 6 pages.

*Primary Examiner* — Gene O Crawford
*Assistant Examiner* — Kelvin L Randall, Jr.
(74) *Attorney, Agent, or Firm* — Taft Stettinius & Holliser LLP; Ryan O. White

(57) ABSTRACT

A product dispensing apparatus that dispenses feminine products. This machine functions by having two pushbuttons on the front of the cabinet which when pushed, force a feminine product onto the release tray for a user to reach. Inside the cabinet is a time delay mechanically operated system that allows the operator of the invention to control the amount of time between allowable release of products. The operator of the machine can control the amount of time from a minimum of one (1) second between allowable release to thirty (30) seconds between allowable release.

2 Claims, 10 Drawing Sheets

(56) References Cited

U.S. PATENT DOCUMENTS

| | | | | |
|---|---|---|---|---|
| 3,215,481 | A | * | 11/1965 | Kobi ................ A47K 10/28 312/34.15 |
| 3,221,586 | A | * | 12/1965 | Bahnsen .......... A47K 10/3643 225/8 |
| 3,323,848 | A | * | 6/1967 | Bahnsen ............ A47K 10/28 312/34.15 |
| 3,361,996 | A | * | 1/1968 | Goldstein ........... A47K 10/44 335/64 |
| 3,615,041 | A | * | 10/1971 | Bischoff ............ B65D 83/267 222/402.14 |
| 3,858,953 | A | * | 1/1975 | Bahnsen ............ A47K 10/28 312/34.15 |
| 4,308,974 | A | * | 1/1982 | Jones .............. A61F 15/001 221/196 |
| 4,540,107 | A | * | 9/1985 | Davidson ............ A47F 1/10 211/59.2 |
| 4,899,864 | A | | 2/1990 | Van Horn |
| 4,986,524 | A | * | 1/1991 | Meintzer, Jr. ......... B65H 3/10 112/113 |
| 5,167,345 | A | | 12/1992 | Bleeker |
| 6,215,079 | B1 | * | 4/2001 | Hagleitner ........... G04F 3/025 200/33 R |
| 7,469,779 | B2 | | 12/2008 | Horian |
| 7,950,513 | B2 | | 5/2011 | Horian |
| 9,721,419 | B1 | | 8/2017 | Morad et al. |
| 2004/0089670 | A1 | * | 5/2004 | Goeking .............. A47F 1/10 221/123 |
| 2006/0266616 | A1 | | 11/2006 | Nakashima |
| 2010/0170915 | A1 | * | 7/2010 | Reinsel ............... A47F 1/10 221/279 |
| 2011/0000760 | A1 | | 1/2011 | Lacroix-Toyne |
| 2013/0032609 | A1 | * | 2/2013 | Righetti .............. A47F 1/10 221/103 |

* cited by examiner

MECHANICAL TIME DELAY PRODUCT DISPENSER

BACKGROUND OF THE INVENTION

1. Field of the Invention

The present invention relates to vending machines that dispense feminine products. Specifically, this invention relates to pushbutton mechanically operated machines that dispense feminine products.

2. Description of the Prior Art

There are coin drop mechanisms and coin-operated release machines in various forms in the prior art. These previous inventions vary in sophistication and efforts to prevent against theft, weather conditions, and durability. Numerous inventions within the prior art prevent fraud by having complex electronic or mechanical schemes to authenticate currency. Other less complex coin drop mechanisms or coin-operated release machines require the user to rotate a handle by twisting a rotatable lever. The Americans with Disabilities Act (ADA) requires operable parts of fixed elements to not require the user to tightly grasp, pinch, or twisting of the wrist, or more than 5 pounds of force (lbf) to operate.

The following two (2) patents are relevant to the present invention:

1. U.S. Pat. No. 7,469,779 issued to James G. Horian on Dec. 30, 2008 for "Coin Drop Mechanism" (hereafter "the Horian 2008 Patent");
2. U.S. Pat. No. 7,950,513 issued to James G. Horian on May 31, 2011 for "Coin Drop Mechanism" (hereafter the "Horian 2011 Patent"); and The products disclosed in the above two (2) patents are not in full compliance with the AD. Therefore, there is a significant need for an improved product dispensing machine over the prior art that is in compliance with the ADA.

SUMMARY OF THE INVENTION

The present invention is a product dispensing machine that dispenses feminine products. This machine functions by having two pushbuttons on the front of the cabinet that operate by being pushed, to force a feminine product onto a release tray for a user easily grasp and remove the feminine product. Inside each cabinet is a mechanically operated time delay system that allows the operator of the invention to control the amount of time between allowable release of products. The operator of the machine can control the amount of time from a minimum of one (1) second between allowable release of feminine product to thirty (30) seconds between allowable release of feminine product.

The present invention is unique because it contains a pushbutton release coupled with a mechanical delay. Electronic delays are known in the prior art. However, these require batteries or power to operate. The mechanical delay of the present invention is unique because it prevents a user from emptying the machine of free products within a short period of time without the use of an electronic delay.

Another advantage of the present invention is that it provides a mechanically operated time delay coupled with a pushbutton release without requiring a user to twist or apply torque to any portion of the machine to obtain the dispensed feminine product.

The mechanical functioning components of the present invention and the products to be dispensed are primarily found within the present invention's cabinet interior. The external components of the present invention such as the release tray and the moveable pushbuttons are found on the front of the invention.

It is an object of the present invention to provide an apparatus to hold and dispense two products and comply with The Americans with Disabilities Act (ADA) requirements. These two products are sanitary napkins and tampons but it is within the spirit and scope of this invention for this machine to have the capability to dispense similarly sized products. The pushbutton release mechanisms used to release these two products are the same.

It is a further object of the present invention to provide a predominantly mechanical device for dispensing feminine products that does not require the rotation of a handle. This can be difficult or impossible for individuals with physical limitations.

It is an additional object of the present invention to allow the operator or owner of the present invention to control the amount of time between allowable release of a product. Since this present invention is designed to be for a free product, it is desirable for there to be a time delay between the release of products. This is done to prevent a user from taking all of the products from the machine in a short amount of time.

It is an additional object of the present invention to provide a simple mechanical device that dispenses feminine products for free with a time delay that is not electronic. This mechanical time delay, as opposed to an electronic time delay, allows the present invention to function without the need of batteries or power. This reduces the cost of operation and maintenance.

Further novel features and other objects of the present invention will become apparent from the following detailed description, discussion and the appended claims, taken in conjunction with the drawings.

BRIEF DESCRIPTION OF THE DRAWINGS

Referring particularly to the drawings for the purpose of illustration only and not limitation, there is illustrated.

DETAILED DESCRIPTION OF EMBODIMENTS OF THE PRESENT INVENTION

Although specific embodiments of the present invention will now be described with reference to the drawings, it should be understood that such embodiments are by way of example only and merely illustrative of but a small number of the many possible specific embodiments which can represent applications of the principles of the present invention. Various changes and modifications obvious to one skilled in the art to which the present invention pertains are deemed to be within the spirit, scope and contemplation of the present invention as further defined in the appended claims.

Figure 1:
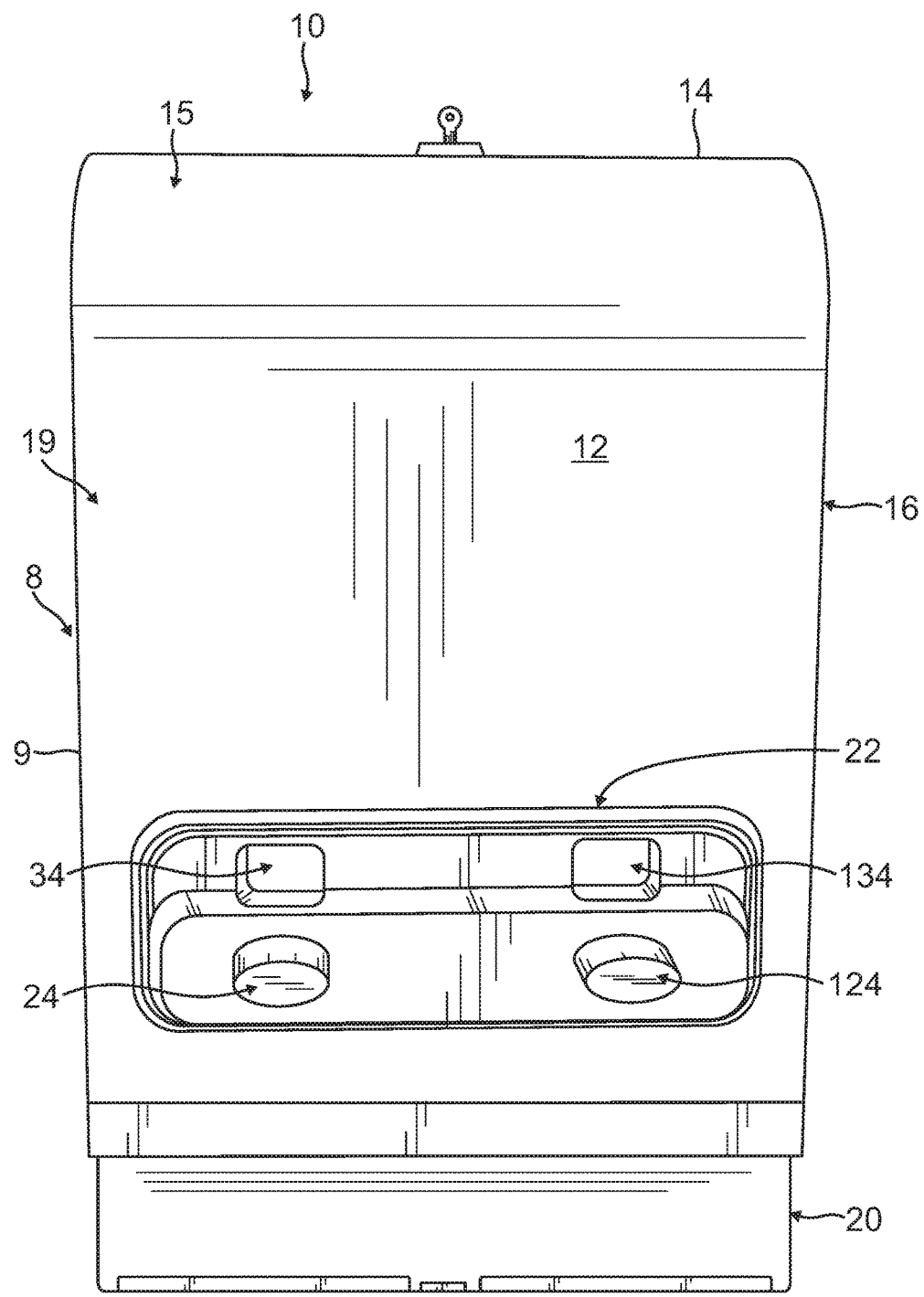
FIG. 1 is a front elevational view of the present invention with the door to the invention in the closed position.
Figure 2:
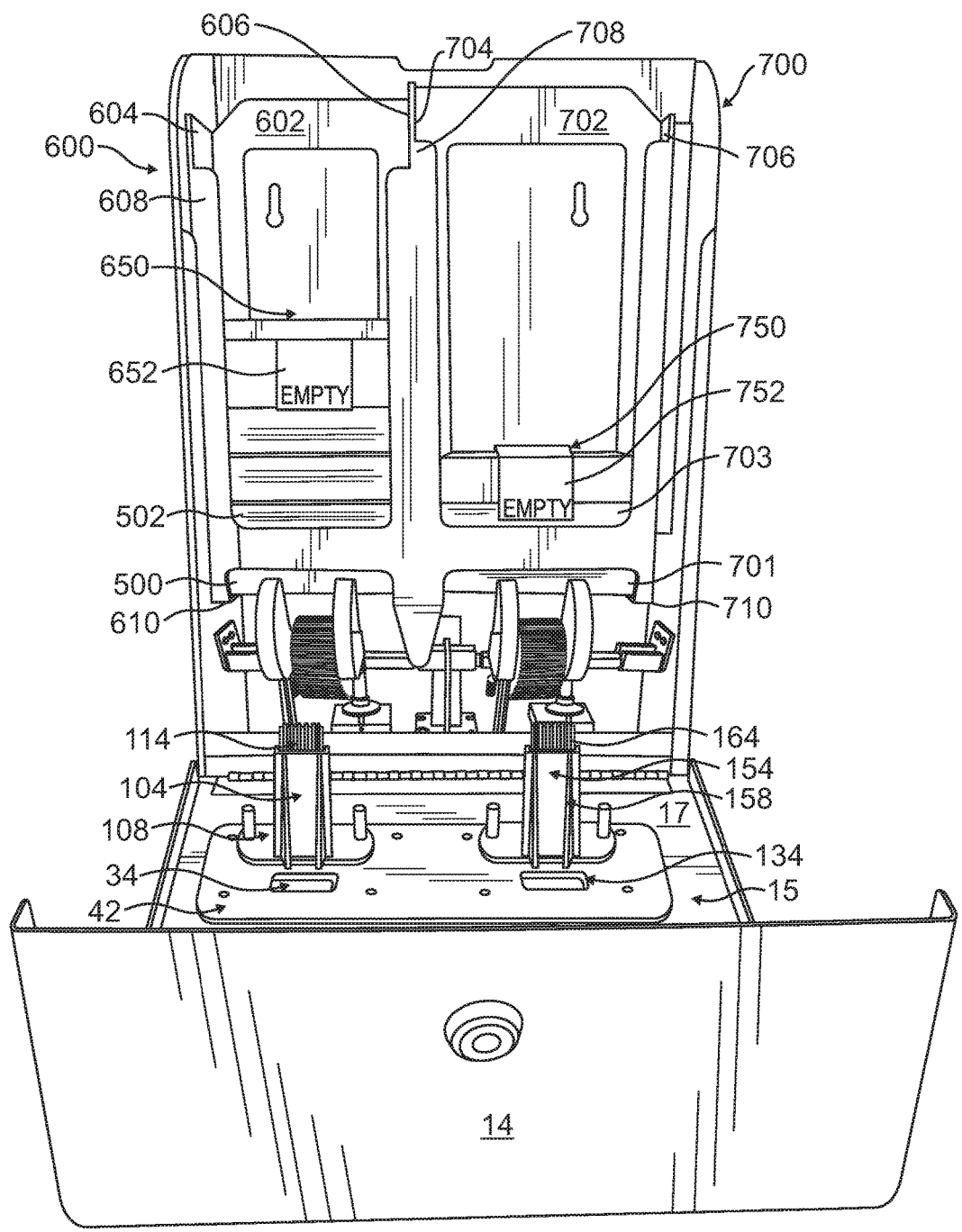
FIG. 2 is a front perspective view of the present invention with the door to the invention open.

Referring to FIGS. 1 and 2, there is illustrated a front elevational view of the present invention time delay product dispenser 10 with its front door 19 closed. The present invention is comprised of internal components contained within cabinet 8. There is a left internal system which functions independently but identically to the right internal system. The left internal system allows a user to access sanitary napkins and the right internal system allows a user to access tampons.

Cabinet 8 is comprised of a top panel 14, a left side panel 9, a right side panel 16, a bottom panel 3 with a bottom release tray 20, a front panel 15, and a back panel 18. Located towards the bottom of front panel 15 on front face 12 of front panel 15 there is front face plate 22. Front face plate 22 has a left pushbutton 24 to release sanitary napkins and a right pushbutton 124 to release tampons. Located directly above left pushbutton 24 on front face plate 22 is a left window 34. Similarly, located directly above right pushbutton 124 on front face plate 22 is a right window 134. During operation a user has the ability to press in left pushbutton 24 to release a sanitary napkin or to press in right pushbutton 124 to release a tampon.

Referring to FIG. 2, there is illustrated the present invention time delay product dispenser 10 in the open position with front panel 15 pivoted outward. Within time delay product dispenser 10 is sanitary napkin rack 600 and tampon rack 700. Sanitary napkin rack 600 has a sanitary napkin rack back 602, sanitary napkin rack left side 604, sanitary napkin rack right side 606, a sanitary napkin rack front 608, and sanitary napkin rack bottom 610. Tampon rack 700 has a tampon rack back 702, tampon rack left side 704, tampon rack right side 706, a tampon rack front 708, and tampon rack bottom 710.

Figure 3:
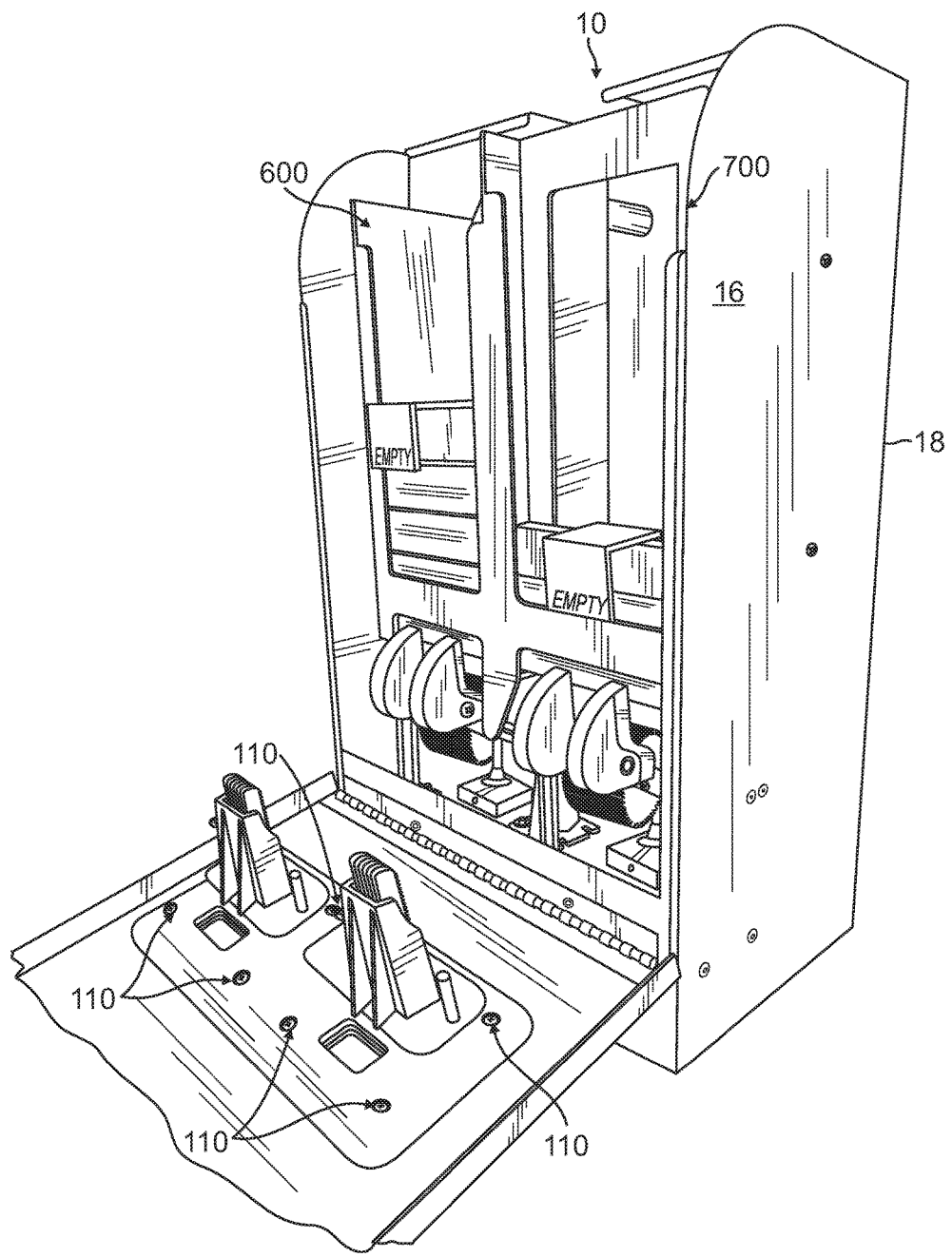
FIG. 3 is a front perspective view of the present invention with the door to the invention open and the invention rotated approximately 45 degrees from the view of FIG. 2.

Referring to FIGS. 2 and 3, rear face plate 42 is affixed to back surface 17 of front panel 15 by eight (8) screws 110. Screws 110 also affix front face plate 22 to front panel 15. Only six of the eight screws are illustrated in FIG. 3.

Sanitary Napkin Dispensing

Figure 4:
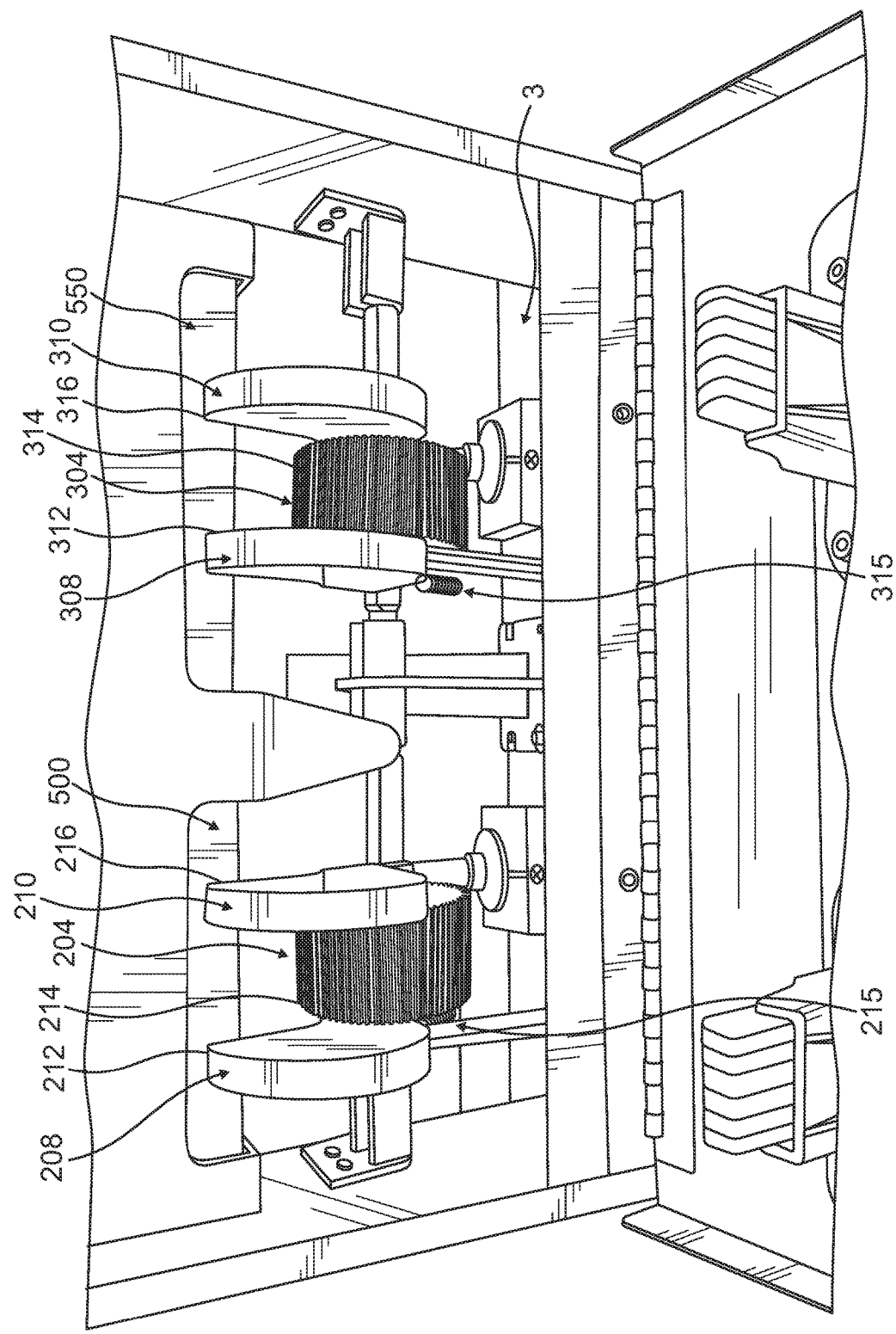
FIG. 4 is a zoomed in front perspective view of the present invention with the door to the invention open.
Figure 5:
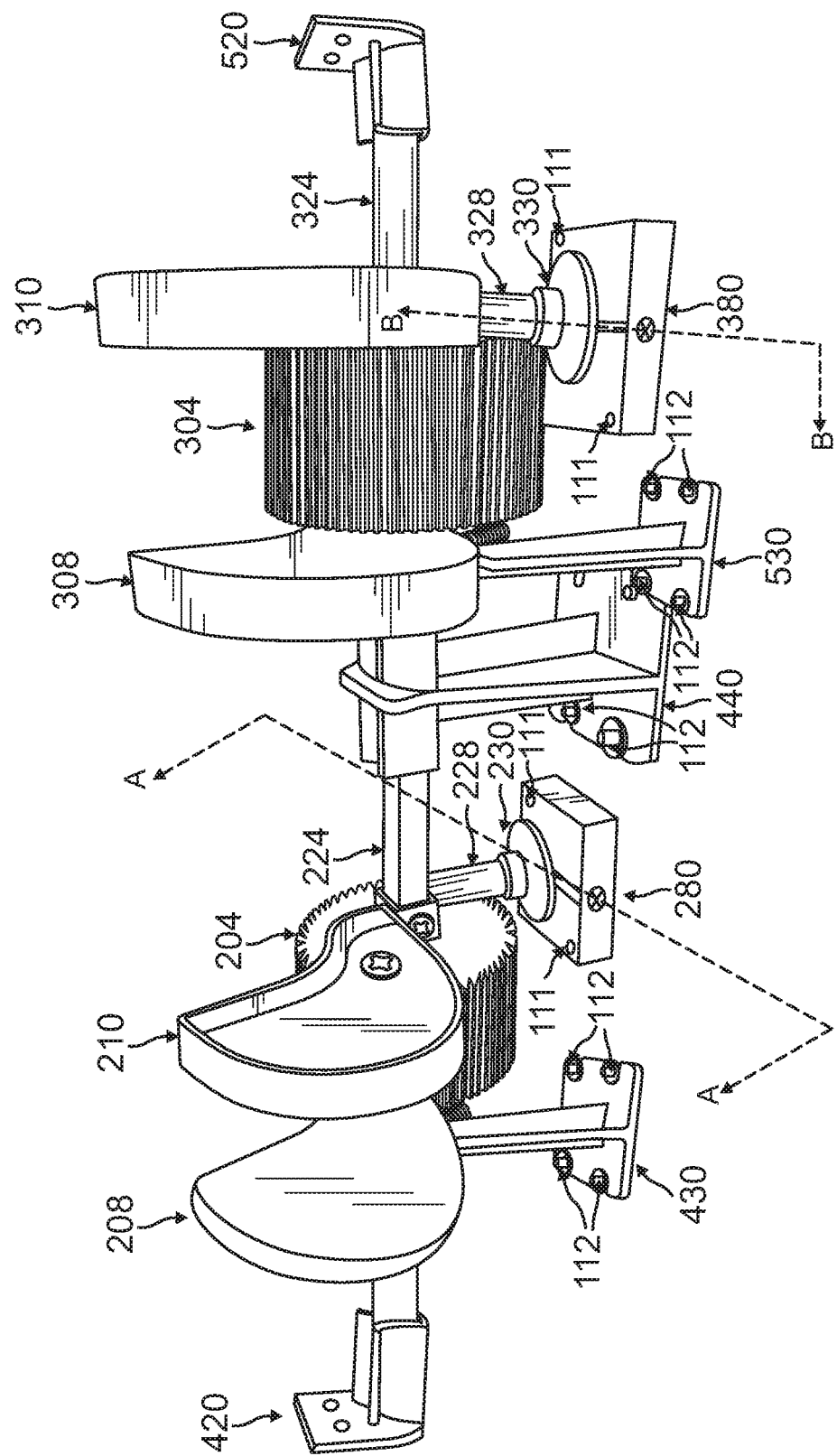
FIG. 5 is a zoomed in front perspective view of the lower internal components of the present invention without the cabinet.

Referring to FIGS. 4 and 5, inside time delay product dispenser 10 and near bottom release tray 20 (see FIG. 1) is left horizontal support rod 224 which is supported on the left end by left end support 420 and on the right end by center support 440. Left horizontal support rod 224 (also called left horizontal support member) passes through the center of left pinon gear 204 and provides an axis by which left pinon gear 204 may rotate in the clockwise and counterclockwise direction. First left wing 208 and left pinon gear 204 are prevented from rotating past the initial resting condition in the counterclockwise direction by left stopper post 430. Similarly, first right wing 308 and right pinon gear 304 are prevented from rotating past the initial resting condition in the counterclockwise direction by right stopper post 530. (The wings are also called sanitary napkin members.)

Figure 6:
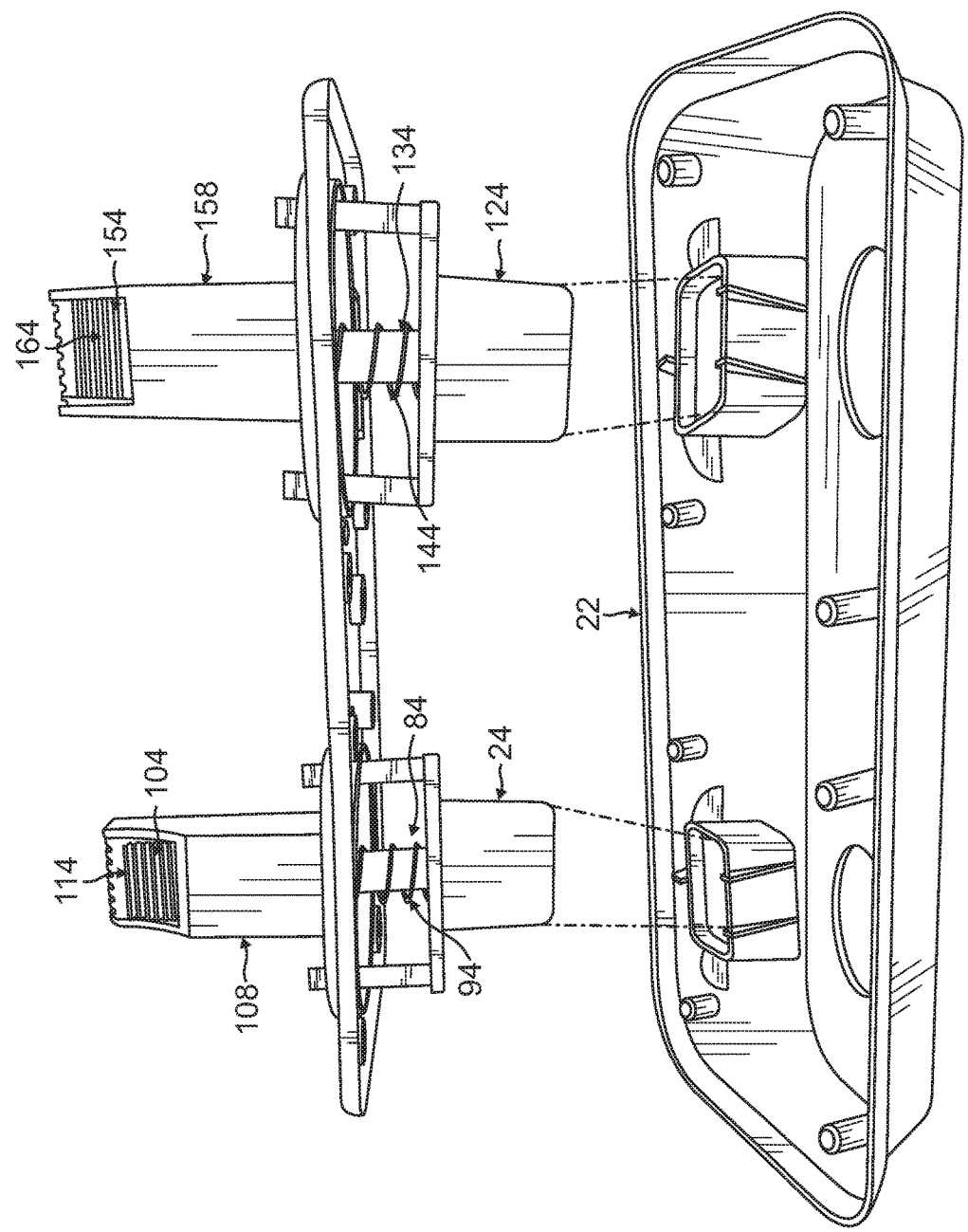
FIG. 6 is an exploded view of the front face plate with respective pushbuttons, push rods, push rod connectors, and push compression springs.

Referring to FIGS. 1 and 2, during operation when a user presses left pushbutton 24 (also called left activation member) inwards towards the center of time delay product dispenser 10, left push rod 104 located inside of left housing 108, which is integrally affixed to left pushbutton 24 by left push rod connector 84 (see FIG. 6), simultaneously moves inwards towards the center of time delay product dispenser 10. Referring to FIG. 6, when left push rod 104 moves inwards, this simultaneously causes left push rod teeth 114 that are interlocked with left pinon gear teeth 214 of left pinon gear 204 to rotate in the clockwise direction and left push compression spring 94 to compress. Integrally affixed to left pinon gear 204 is first left wing 208 and second left wing 210. First left wing 208 has a first left wing front surface 212 that is in direct contact with lowest sanitary napkin 500. Similarly, second left wing 210 has a second left wing front surface 216 that is also in direct contact with lowest sanitary napkin 500. Thus, when left pushbutton 24 is pressed in towards the center of time delay product dispenser 10 to a distance of approximately 0.5 inches this causes left pinion gear 204 to rotate approximately 20 degrees which causes first left wing 208 and second left wing 210 to push lowest sanitary napkin 500 off sanitary napkin rack 600 and on to bottom release tray 20.

When lowest sanitary napkin 500 has been pushed off sanitary napkin rack bottom 610, second lowest sanitary napkin 502 is pushed down by the weight of sanitary napkin weight 650 and becomes lowest sanitary napkin 500. This process is repeated until all of the sanitary napkins are removed from time delay product dispenser 10. When all of the sanitary napkins are removed from time delay product dispenser 10, sanitary napkin weight front face 652 displays through window 34 and reads "Empty" to signal to the user that this product is no longer available.

Figure 7:
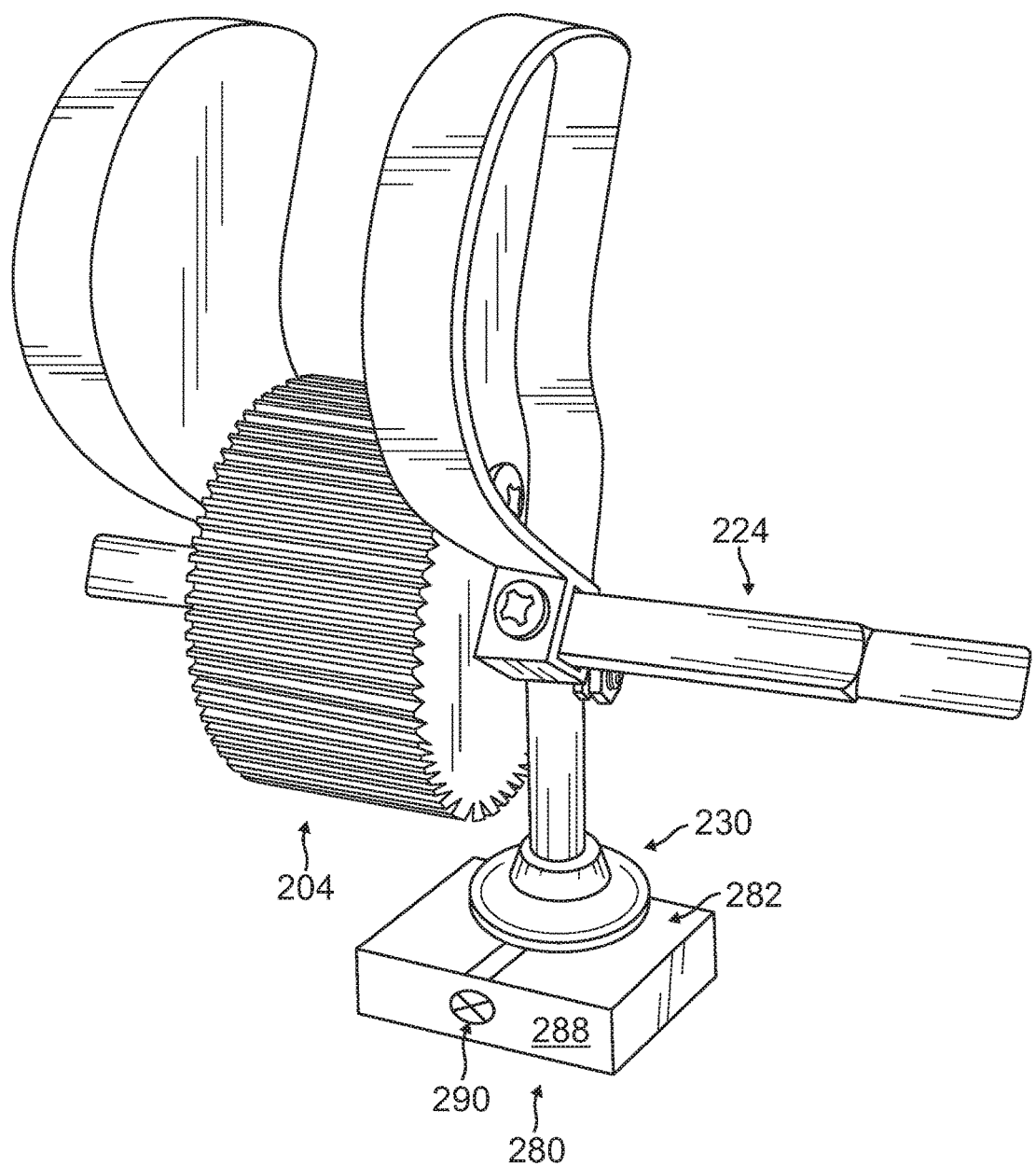
FIG. 7 is a zoomed in view of the left pinon gear rotated after left pushbutton has been pressed with left plunger temporarily affixed to a left timing plate.
Figure 9:
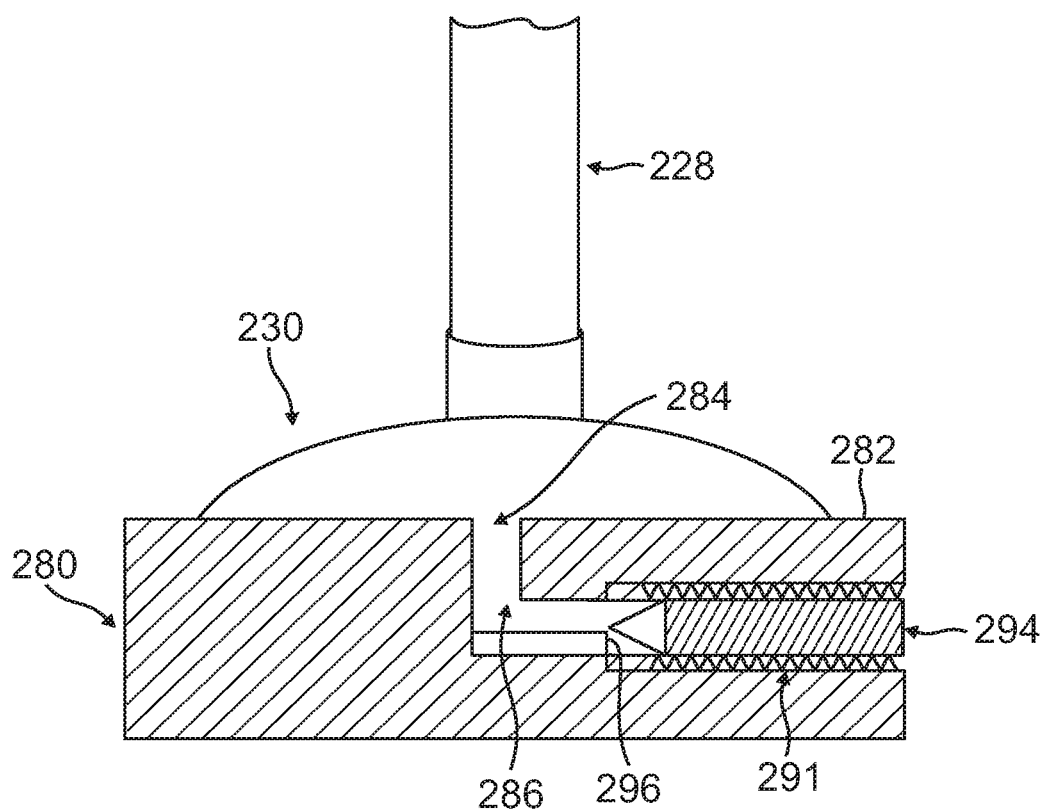
FIG. 9 is cross sectional view A-A as shown in FIG. 5 that shows left plunger temporarily affixed to left timing plate and a threaded screw inserted to a maximum distance to create the longest delay for the resetting of left pushbutton.
Figure 10:
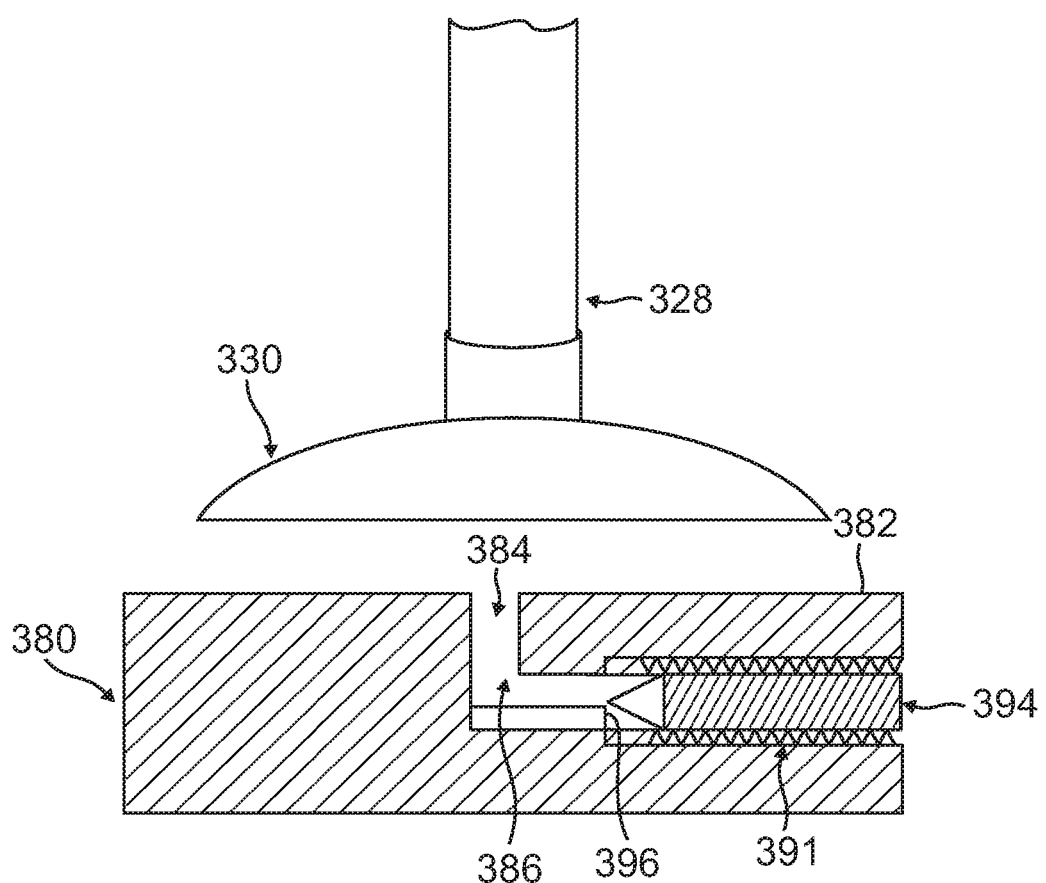
FIG. 10 is a partial view of cross section B-B as shown in FIG. 5 that shows right plunger in the initial condition prior to the right pushbutton being pressed by user and right timing plate and right threaded screw inserted to a maximum distance to create the longest delay for the resetting of the right pushbutton.

Referring to FIG. 5, left horizontal support rod 224 and left vertical plunger rod 228 are affixed to left pinon gear 204. Affixed to the distal end of left vertical plunger rod 228 is left plunger 230. When left pushbutton 24 is pressed in towards the center of time delay product dispenser 10 to a distance of approximately 0.5 inches this causes left pinion gear 204 to rotate approximately 20 degrees. This action further causes left vertical plunger rod 228 and left plunger 230 to displace downwards and cause left plunger 230 to be temporarily affixed to left timing plate 280 (as shown in detail in FIGS. 7 and 9). Left timing plate 280 is affixed to bottom panel 3 of cabinet 8 by two (2) screws 111. Left timing plate 280 has a left top surface 282 that contains a top circular hole 284 that is directly connected to left interior chamber 286. Left timing plate 280 also has a left front surface 288 that has a left front circular hole 290 (see FIG. 7) that connects to left interior chamber 286. Within left interior chamber 286, adjacent to left front circular hole 290, are left internal threads 291 that receive left threaded screw 294. Left interior chamber 286 also contains left interior endwall 296 that acts as a stopper for left threaded screw 294. While left plunger 230 is temporarily affixed to left timing plate 280, left pushbutton 24 is not operational. Left plunger 230 must be in the air and/or elevated and not temporarily affixed to left timing plate 280 for left pushbutton 24 to be operational.

Referring to FIGS. 4, 5, 6 and 9, the operator of this machine has the ability to increase or decrease the amount of time between left pushbutton 24 resetting, becoming operational when left plunger 230 is released and no longer temporarily affixed to left timing plate 280. The amount of time that left plunger 230 is temporarily affixed to left timing plate 280 is controlled by the amount of air within left interior chamber 286. The greater the amount of air located in left interior chamber 286, the shorter the time period that left plunger 230 will be affixed to left timing plate 280. The operator of the machine has the ability to increase or decrease the amount of air within left interior chamber 286 by tightening or loosening left threaded screw 294. When left threaded screw 294 is entirely inserted into interior chamber 286, the reset time for left pushbutton 24 to become operational again is at a maximum which is approximately 30 seconds. When left threaded screw 294 is entirely removed from left interior chamber 236 the reset time for left pushbutton 24 to become operational again is at a minimum which is approximately one (1) second. The operator has the ability to control the amount of time between left pushbutton 24 resetting by the amount of air inside left interior chamber 286 which is controlled by how far left threaded screw 294 is inserted into left interior chamber 286 by use of left internal threads 291.

When left pushbutton 24 has been pressed and left pinion gear 204 has been rotated approximately 20 degrees in the clockwise direction to cause left plunger 230 to come in contact with left timing plate 280, left tension spring 215 is also put in tension. In this state there are two rotational forces being applied to left pinion gear 204. There is a clockwise force being applied by left plunger 230 and a counterclockwise force being applied by left tension spring 215. After enough air has passed under left plunger 230 to reduce the affixing force between left plunger 230 and left timing plate 280, the counterclockwise rotational force of left tension spring 215 becomes the more dominant force and causes first left wing 208, left pinion gear 204, and second left wing 210 to rotate in the counterclockwise direction and thus returning left pushbutton 24 to reset or to be returned to its initial starting condition and become ready for use by a user.

Tampon Dispensing

Referring to FIG. 5, inside time delay product dispenser 10 and near bottom release tray 20 is right horizontal support rod 324 which is supported on the right end by right end support 520 and on the left end by center support 440. Right horizontal support rod 324 passes through the center of right pinon gear 304 and provides an axis by which right pinon gear 304 may rotate in the clockwise and counterclockwise direction. First right wing 308 and right pinon gear 304 are prevented from rotating past the initial resting condition in the counterclockwise direction by right stopper post 530.

Referring to FIG. 4, during operation when a user presses right pushbutton 124 (also called right activation member) inwards towards the center of time delay product dispenser 10, right push rod 154 located inside of right housing 158, which is integrally affixed to right pushbutton 124 by right push rod connector 144, simultaneously moves inwards towards the center of time delay product dispenser 10. When right push rod 154 moves inwards, this simultaneously causes right push rod teeth 164 that are interlocked with right pinon gear teeth 314 of right pinion gear 304 to rotate in the clockwise direction and causes right push compression spring 144 to compress. Integrally affixed to right pinon gear 304 is first right wing 308 and second right wing 310 (see FIG. 4). First right wing 308 has a first right wing front surface 312 that is in direct contact with lowest tampon 701. Similarly, second right wing 310 has a second right wing front surface 316 that is also in direct contact with lowest tampon 701 (also called tampon member). Therefore, when right pushbutton 124 is pressed in towards the center of time delay product dispenser 10 to a distance of approximately 0.5 inches this causes right pinion gear 304 to rotate approximately 20 degrees which causes first right wing 308 and second right wing 310 to push lowest tampon 701 off tampon rack 700 and on to bottom release tray 20.

When lowest tampon 701 has been pushed off tampon rack bottom 710, second lowest tampon 703 is pushed down by the weight of tampon weight 750 and becomes lowest tampon 701. This process is repeated until all of the tampons are removed from time delay product dispenser 10. When all of the tampons are removed from time delay product dispenser 10 tampon weight front face 752 displays through right window 134 and reads "Empty" to signal to the user that this product is no longer available.

Figure 8:
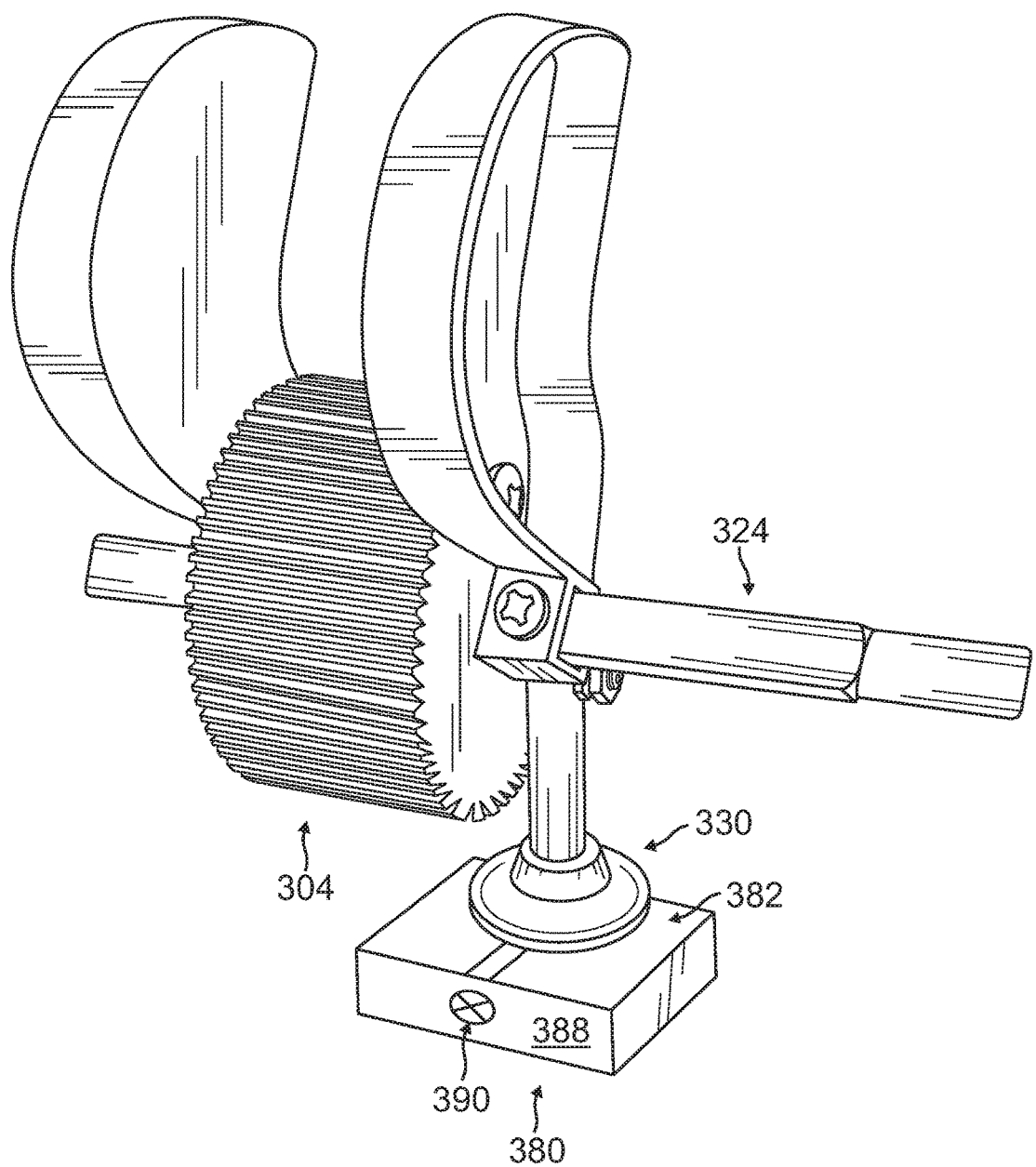
FIG. 8 is a zoomed in view of the right pinon gear rotated after left pushbutton has been pressed with left plunger temporarily affixed to a left timing plate.

Referring to FIGS. 4, 5, 6 and 10, right horizontal support rod 324 and right vertical plunger rod 328 are affixed to right pinon gear 304. Affixed to the distal end of right vertical plunger rod 328 is right plunger 330. When right pushbutton 124 is pressed in towards the center of time delay product dispenser 10 to a distance of approximately 0.5 inches this causes right pinion gear 304 to rotate approximately 20 degrees. This action further causes right vertical plunger rod 328 and right plunger 330 to displace downwards and cause right plunger 330 to be temporarily affixed to right timing plate 380 (see FIGS. 8 and 10). Right timing plate 380 affixed to bottom panel 3 of cabinet 8 by two (2) screws 111. Right timing plate 380 has a right top surface 382 that contains a right top circular hole 384 that is directly connected to right interior chamber 386. Right timing plate 380 also has a right front surface 388 that has a right front circular hole 390 that connects to right interior chamber 386. Within right interior chamber 386, adjacent to right front circular hole 390 (see FIG. 10), are right internal threads 391 that receive right threaded screw 394. Right interior chamber 386 also contains right interior endwall 396 that acts as a stopper for right threaded screw 394. While right plunger 330 is temporarily affixed to right timing plate 380, right pushbutton 124 is not operational. Right plunger 330 must be in the air and/or elevated and not temporarily affixed to right timing plate 380 for right pushbutton 124 to be operational.

Referring to FIGS. 4, 5, 6 and 10, the operator of this machine has the ability to increase or decrease the amount of time between right pushbutton 124 resetting and becoming operational when right plunger 330 is released and no longer temporarily affixed to timing plate 380. The amount of time that right plunger 330 is temporarily affixed to right timing plate 380 is controlled by the amount of air within interior chamber 386. The greater the amount of air located within right interior chamber 386, the shorter the time period that plunger 330 will be affixed to right timing plate 380. The operator of the machine has the ability to increase or decrease the amount of air within right interior chamber 386 by tightening or loosening right threaded screw 394. When right threaded screw 394 is entirely inserted into right interior chamber 386, the reset time for right pushbutton 124 to become operational again is at a maximum which is approximately 30 seconds. When right threaded screw 394 is entirely removed from right interior chamber 336 the reset time for right pushbutton 124 to become operational again is at a minimum which is approximately one (1) second. The operator has the ability to control the amount of time between right pushbutton 124 resetting by the amount of air inside right interior chamber 386 which is controlled by how far right threaded screw 394 is inserted into right interior chamber 386 by use of right internal threads 391.

When right pushbutton 124 has been pressed and right pinion gear 304 has been rotated approximately 20 degrees in the clockwise direction to cause right plunger 330 to come in contact with right timing plate 380, right tension spring 315 is also put in tension. In this state there are two rotational forces being applied to right pinion gear 304. There is a clockwise force being applied by right plunger 330 and a counterclockwise force being applied by right tension spring 315. After enough air has passed under right plunger 330 to reduce the affixing force between right plunger 330 and right timing plate 380, the counterclockwise rotational force of right tension spring 315 becomes the more dominant force and causes first right wing 308, right pinion gear 304, and second right wing 310 to rotate in the counterclockwise direction and thus returning right pushbutton 124 to reset or to be returned to its initial starting condition and become ready for use by a user.

Of course the present invention is not intended to be restricted to any particular form or arrangement, or any specific embodiment, or any specific use, disclosed herein, since the same may be modified in various particulars or relations without departing from the spirit or scope of the claimed invention herein above shown and described of which the apparatus or method shown is intended only for illustration and disclosure of an operative embodiment and not to show all of the various forms or modifications in which this invention might be embodied or operated.

What is claimed is:

1. An apparatus to retain and dispense feminine products, the apparatus comprising:
   a. a cabinet comprising a top panel, a left side panel, a right side panel, a front panel, a back panel, and a bottom panel with said bottom panel having a bottom release tray;
   b. said front panel comprising a front face, a front face plate with said front face plate having a left pushbutton and a right pushbutton;
   c. a sanitary napkin rack and a tampon rack with said sanitary napkin rack having a sanitary napkin rack back, a sanitary napkin rack left side, a sanitary napkin rack right side, a sanitary napkin rack front, and a sanitary napkin rack bottom, and said tampon rack having a tampon rack back, a tampon rack left side, a tampon rack right side, a tampon rack front, and a tampon rack bottom;
   d. a left horizontal support rod that is affixed through a center of a left pinion gear and a right horizontal support rod that is affixed through a center of a right pinion gear;
   e. said left horizontal support rod is affixed at a distal end to a left plunger and said right horizontal support rod is affixed at a distal end to a right plunger;
   f. said bottom panel having a left timing plate and a right timing plate affixed to said bottom panel;
   g. said left timing plate having a left top surface and a left front surface with said left top surface having a left top circular hole that is directly connected to a left interior chamber;
   h. said right timing plate having a right top surface and a right front surface with said right top surface having a right top circular hole that is directly connected to a right interior chamber;
   i. said left interior chamber having left internal threads adjacent to a left front circular hole and said right interior chamber having right internal threads adjacent to a right front circular hole;
   j. said left timing plate configured to enable said left interior chamber to be decreased in size as a left threaded screw engages said left internal threads and is further inserted into said left front circular hole with a suction release timing on said left plunger that is increased as a volume of air in the left interior chamber is reduced as the left threaded screw is threaded further into the left timing plate; and
   k. said right timing plate configured to enable said right interior chamber to be decreased in size as a right threaded screw engages said right internal threads and is further inserted into said right front circular hole with a suction release timing on said right plunger that is increased as a volume of air in the right interior chamber is reduced as the right threaded screw is threaded further into the right timing plate;
   l. whereby, when the left pushbutton is pressed in towards a center of said cabinet, a left push rod moves causing teeth on said left push rod to engage teeth on said left pinion gear causing a first left wing and a second left wing to rotate and push a lowest sanitary napkin off said sanitary napkin rack and onto said bottom release tray while causing a left vertical plunger rod and said left plunger to displace downwards and cause said left plunger to be temporarily affixed to said left timing plate, with a length of time to reset the left pushbutton to dispense another sanitary napkin dependent on the suction release timing of the left plunger before it is released;
   m. whereby, when the right pushbutton is pressed in towards the center of said cabinet, a right push rod moves causing teeth on said right push rod to engage teeth on said right pinion gear causing a first right wing and a second right wing to rotate and push a lowest tampon off said tampon rack and onto said bottom release tray while causing a right vertical plunger rod and said right plunger to displace downwards and cause said right plunger to be temporarily affixed to said right timing plate, with a length of time to reset the right pushbutton to dispense another tampon is dependent on the suction release timing of the right plunger before it is released.

2. The apparatus in accordance with claim 1, further comprising:
   a. said left plunger is temporarily affixed to said left timing plate for a period of time between one second to thirty seconds; and
   b. said right plunger is temporarily affixed to said right timing plate for a period of time between one second to thirty seconds.

* * * * *